US00PP19042P2

(12) United States Plant Patent
Trees

(10) Patent No.: US PP19,042 P2
(45) Date of Patent: Jul. 22, 2008

(54) ***GERANIUM* PLANT NAMED 'BALGALDEPRO'**

(50) Latin Name: *Pelargonium×hybrida*
Varietal Denomination: Balgaldepro

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 45 days.

(21) Appl. No.: 11/605,109

(22) Filed: Nov. 28, 2006

(51) Int. Cl.
*A01H 5/00* (2006.01)

(52) U.S. Cl. ..... Plt./324

(58) Field of Classification Search ..... Plt./324
See application file for complete search history.

(56) References Cited

PUBLICATIONS

Canada Plant Breeders' Rights application No. 06–5291 filed Mar. 9, 2006.
European Plant Breeders' Rights application No. 2003/2257 filed Nov. 8, 2006.

*Primary Examiner*—Annette H Para
(74) *Attorney, Agent, or Firm*—Audrey Charles

(57) ABSTRACT

A new and distinct cultivar of *Geranium* plant named 'Balgaldepro', characterized by its semi-double type dark rose pink-colored flowers, medium green-colored foliage, and minimally vigorous, semi-trailing growth habit.

2 Drawing Sheets

Latin name of genus and species of plant claimed: *Pelargonium×hybrida.*
Variety denomination: 'Balgaldepro'.

BACKGROUND OF THE INVENTION

The present invention relates to a new and distinct cultivar of *Geranium* plant botanically known as *Pelargonium× hybrida* and hereinafter referred to by the cultivar name 'Balgaldepro'.

The new cultivar originated in a controlled breeding program in Arroyo Grande, Calif. during August 2000. The objective of the breeding program was the development of inter-specific *Geranium* cultivars with unique flower and foliage coloration and an outwardly spreading, mounded growth habit.

The new *Geranium* cultivar is an irradiation induced sport of Galleria® Pink Punch 'Balgalpipn', U.S. Plant Pat. No. 11,925, characterized by its semi-double type medium pink-colored flowers, medium green-colored foliage, and semi-trailing growth habit. The irradiation occurred on Aug. 15, 2000. The new cultivar was discovered as a side shoot and selected on January 2001 in a controlled environment at Arroyo Grande, Calif.

Asexual reproduction of the new cultivar by terminal stem cuttings since January 2001 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balgaldepro' as a new and distinct cultivar of *Geranium* plant:

1. Semi-double type dark rose pink-colored flowers;
2. Medium green-colored foliage; and
3. Minimally vigorous, semi-trailing growth habit.

Of the many commercially available *Geranium* cultivars known to the inventor, the most similar in comparison to the new cultivar is the parent Galleria® Pink Punch 'Balgalpipn', U.S. Plant Pat. No. 11,925. However, in side by side comparisons, plants of the new cultivar differ from plants of 'Balgalpipn' in the following characteristics:

1. Plants of the new cultivar have a flower color different from plants of 'Balgalpipn'; and
2. Plants of the new cultivar have longer and wider leaves than plants of 'Balgalpipn'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balgaldepro'. The plants were grown in 4.5 inch pots for 7 weeks in a greenhouse at West Chicago, Ill.

DETAILED BOTANICAL DESCRIPTION

Figure 1:
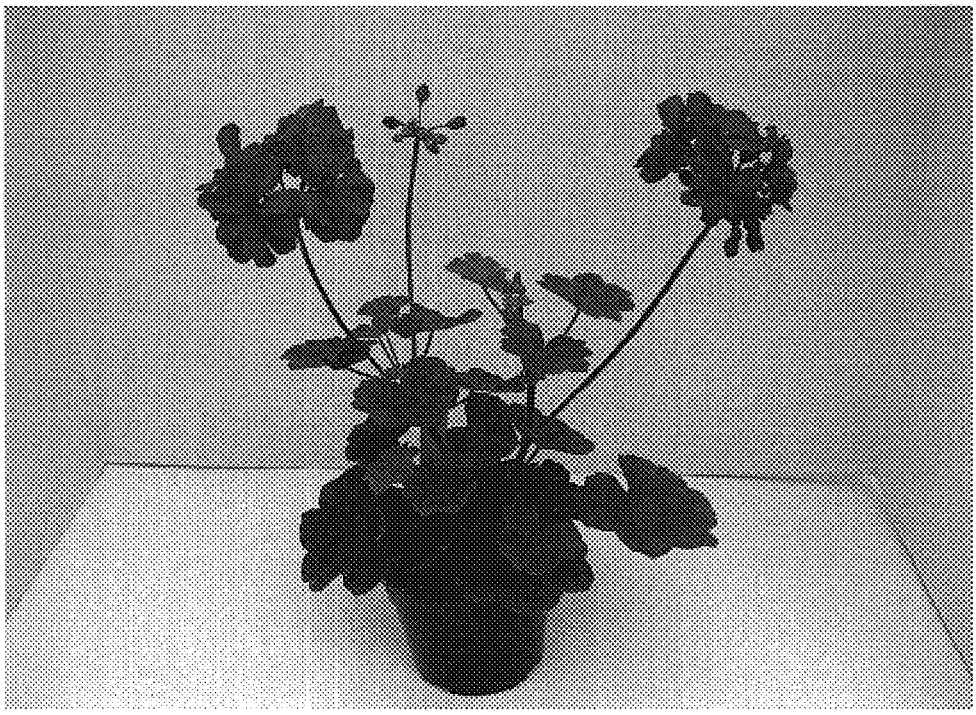
FIG. 1 illustrates a side view of the overall growth and flowering habit of 'Balgaldepro'.
Figure 2:
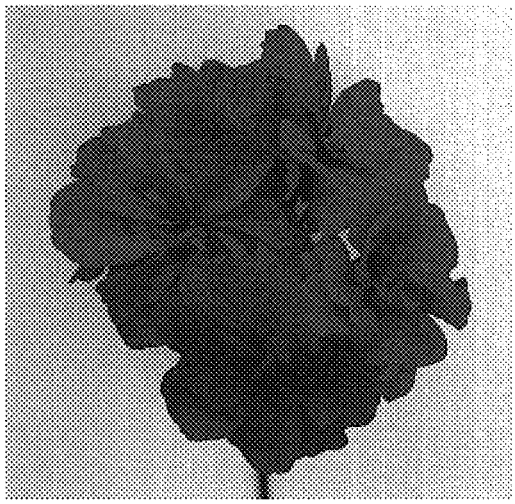
FIG. 2 illustrates a close-up view of an individual umbel of 'Balgaldepro'.
Figure 3:
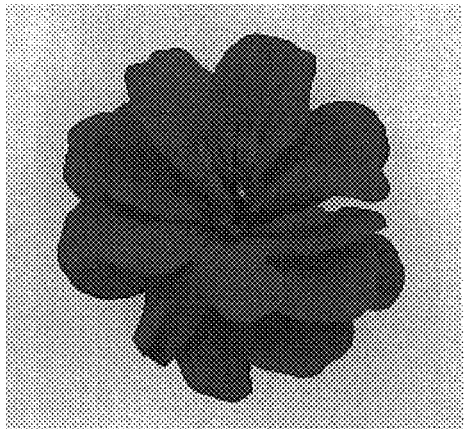
FIG. 3 illustrates a close-up view of an individual flower of 'Balgaldepro'.
Figure 4:
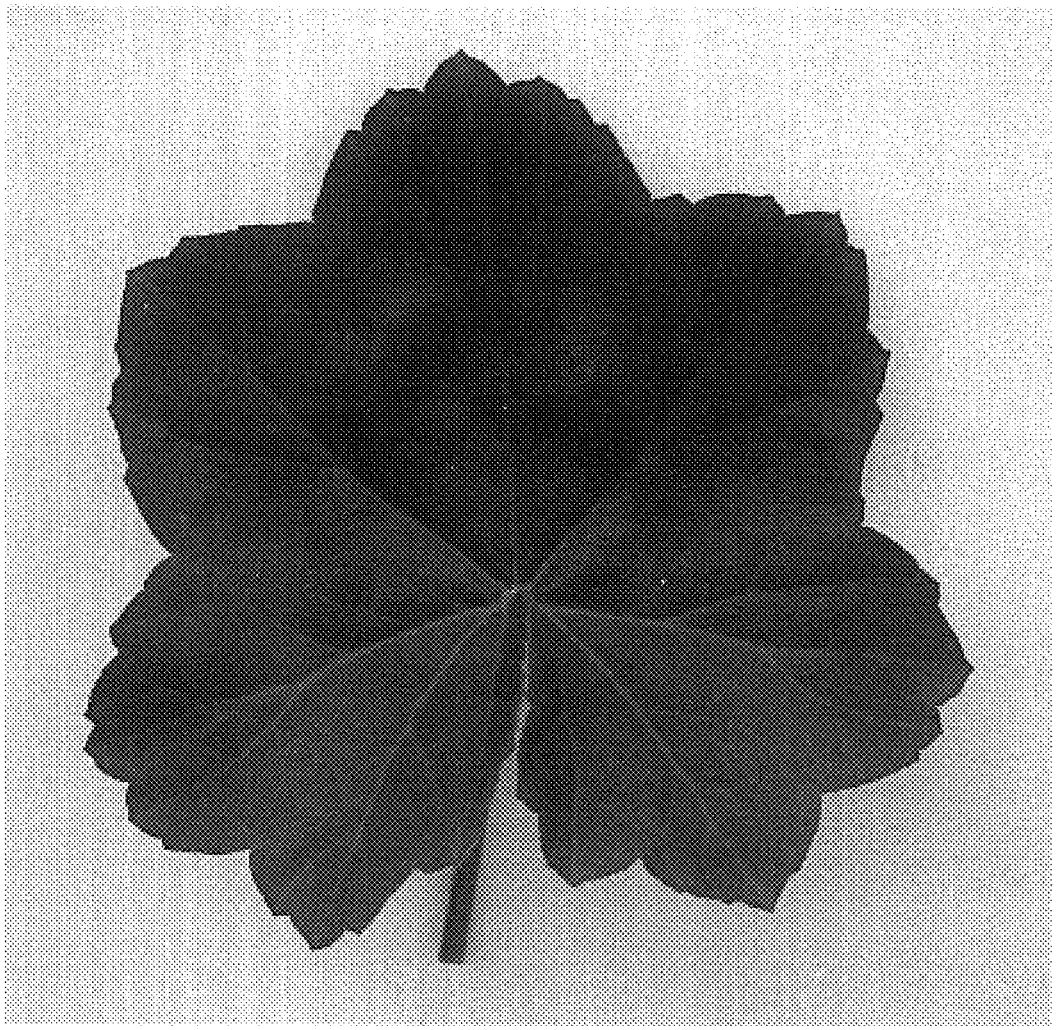
FIG. 4 illustrates a close-up view of an individual leaf of 'Balgaldepro'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jul. 18, 2006 between 9:00 a.m. and 11:00 a.m. under natural light conditions, in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 7 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Pelargonium×hybrida* cultivar Balgaldepro.

Parentage:

*Parent.*—Galleria® Pink Punch 'Balgalpipn', U.S. Plant Pat. No. 11,925.

Propagation:

*Type cutting.*—Terminal stem.

*Time to initiate roots.*—Approximately 9 to 13 days.

*Time to produce a rooted cutting.*—Approximately 18 to 20 days.

*Root description.*—Fibrous.

*Rooting habit.*—Freely branching.

Plant description:

*Commercial crop time.*—Approximately 8 to 9 weeks from a rooted cutting.

*Growth habit and general appearance.*—Minimally vigorous, upright.

*Size.*—Height from soil level to top of plant plane: Approximately 26.6 cm. Height from soil level to top of foliage: Approximately 18.3 cm. Width: Approximately 24.8 cm.

*Branching habit.*—Freely basal branching. Quantity of main branches per plant: Approximately 2.

*Branch.*—Strength: Strong. Length: Approximately 15.2 cm. Diameter: Approximately 5.0 mm. Length of central internode: Approximately 3.3 cm. Texture: Densely pubescent. Color of young stem: 144A. Color of mature stem: 144A with an overlay of 183D.

Foliage description:

*General description.*—Quantity of leaves per lateral branch: Approximately 11. Fragrance: None. Form: Simple. Arrangement: Opposite.

*Leaves.*—Aspect: Petiole is at an acute angle to stem and blade is perpendicular to stem. Shape: Reniform. Appearance: Shiny. Margin: Crenate, palmately lobed. Apex: Obtuse. Base: Cordate. Venation pattern: Palmate. Length of mature leaf: Approximately 4.8 cm. Width of mature leaf: Approximately 8.4 cm. Texture of upper surface: Pubescent. Texture of lower surface: Pubescent, dense on venation. Color of upper surface of young foliage: 137A with venation of 137A. Color of lower surface of young foliage: 137C with venation of 137C. Color of upper surface of mature foliage: 137A with a very weak zone of 147A and venation of 137A. Color of lower surface of mature foliage: 137B with venation of 137B.

*Petiole.*—Length: Approximately 5.5 cm. Diameter: Approximately 2.3 mm. Texture: Densely pubescent. Color: 137B.

Flowering description:

*Flowering habit.*—'Balgaldepro' is freely flowering under outdoor growing conditions with substantially continuous blooming from spring through autumn and year-round in greenhouse environment.

*Lastingness of individual flower on the plant.*—Approximately 12 to 14 days.

Inflorescences description:

*General description.*—Type: Umbel. Positioned above foliage. Quantity of fully open umbels per plant: Approximately 1. Quantity of developing umbels per plant: Approximately: 2. Fragrance: None. Length or height: Approximately 6.4 cm. Width: Approximately 10.6 cm. Quantity of fully open flowers per inflorescence: Approximately 9.

*Peduncle.*—Strength: Strong. Aspect: Erect. Length: Approximately 15.3 cm. Diameter: Approximately 3.0 mm. Texture: Densely pubescent with a mixture of glandular and nonglandular hairs. Gland color: Colorless, transparent. Color: 144A with an overlay of 183C.

Flower description:

*General description.*—Type: Semi-double.

*Bud.*—Rate of opening: Generally takes 4 to 6 days for bud to progress from first color to fully open flower.

*Bud just before opening.*—Shape: Elliptic. Length: Approximately 1.5 cm. Width: Approximately 9.0 mm. Sepal texture: Densely pubescent with a mixture of glandular and nonglandular hairs. Gland color: Mixture of colorless, transparent; and 29C, transparent. Petal texture: Glabrous. Petal color: Slightly darker than 55A with margin of 45A.

*Corolla.*—Shape: Round. Diameter: Approximately 5.2 cm. Depth: Approximately 2.2 cm.

*Petals.*—Quantity: Approximately 13 petals and 7 irregularly-shaped petaloids per flower. Shape: Obovate. Appearance: Velvety, iridescent. Margin: Entire. Apex: Obtuse. Base: Attenuate. Length of upper petals: Approximately 2.9 cm. Width of upper petals: Approximately 1.5 cm. Length of lower petals: Approximately 2.5 cm. Width of lower petals: Approximately 1.6 cm. Texture of upper and lower surfaces: Glabrous. Color of upper surface of upper petals when fully open: N57A at margin transitioning to N57D at base with central spots of 45A and venation of 71A. Color of lower surface of upper petals when fully open: 55A with venation at base of 71A. Color of upper surface of lower petals when fully open: N57A. Color of lower surface of lower petals when fully open: 55A with venation of 71D.

*Calyx.*—Shape: 5-pointed star. Diameter: Approximately 2.0 cm.

*Sepals.*—Quantity per flower: Approximately 6. Shape: Lanceolate. Margin: Entire. Apex: Acuminate. Base: Fused. Length of upper sepal: Approximately 1.0 cm. Width of upper sepal: Approximately 4.7 mm. Length of lower sepals: Approximately 9.4 mm. Width of lower sepals: Approximately 3.1 mm. Texture of upper surface: Glabrous. Texture of lower surface: Densely pubescent with a mixture of glandular and nonglandular hairs. Gland color: Mixture of colorless, transparent; and 29C, transparent. Color of upper and lower surfaces: 144A with overlay of 187C.

*Pedicel.*—Strength: Strong. Aspect: Acute angle to stem. Length: Approximately 3.2 cm. Diameter: Approximately 1.4 mm. Texture: Densely pubescent with a mixture of glandular and nonglandular hairs. Gland color: Mixture of colorless, transparent; and 29C, transparent. Color: 144A with overlay of 187C.

*Reproductive organs.*—Androecium: Quantity of mature stamens: Approximately 5 per flower. Anther shape: Oblong. Anther length: Approximately 2.0 mm. Anther color: N82A. Pollen amount: Moderate. Pollen color: N30A. Gynoecium: Pistil quantity: 1 per flower. Pistil length: Approximately 1.0 cm. Stigma shape: 5 branched. Stigma length: Approximately 2.0 mm. Stigma color: 187B. Style length: Approximately 3.0 mm. Style color: 160D. Ovary length: Approximately 5.0 mm. Ovary texture: Densely pubescent. Ovary color: 144A.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'Balgaldepro', substantially as herein shown and described.

* * * * *